United States Patent
Talwar et al.

(10) Patent No.: US 9,089,485 B2
(45) Date of Patent: *Jul. 28, 2015

(54) PHARMACEUTICAL COMPOSITIONS OF ENTACAPONE, LEVODOPA AND CARBIDOPA WITH IMPROVED BIOAVAILABILITY

(71) Applicants: Munish Talwar, Aurangabad (IN); Ritesh Kapoor, Ahmedabad (IN); Manoj Mashalkar, Latur (IN); Girish Kumar Jain, Delhi (IN)

(72) Inventors: Munish Talwar, Aurangabad (IN); Ritesh Kapoor, Ahmedabad (IN); Manoj Mashalkar, Latur (IN); Girish Kumar Jain, Delhi (IN)

(73) Assignee: Wockhardt Ltd., Bandra East, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/194,685

(22) Filed: Mar. 1, 2014

(65) Prior Publication Data

US 2014/0187644 A1    Jul. 3, 2014

Related U.S. Application Data

(63) Continuation of application No. 12/865,745, filed as application No. PCT/IB2009/050486 on Feb. 6, 2009, now Pat. No. 8,709,485.

(30) Foreign Application Priority Data

Feb. 6, 2008  (IN) ........................ IN2008MU262A
Feb. 6, 2008  (IN) ........................ IN2008MU263A

(51) Int. Cl.
| | | |
|---|---|---|
| *A61K 9/14* | (2006.01) | |
| *A61K 9/20* | (2006.01) | |
| *A61K 31/195* | (2006.01) | |
| *A61K 31/198* | (2006.01) | |
| *A61K 31/275* | (2006.01) | |
| *A61K 31/277* | (2006.01) | |
| *A61K 9/16* | (2006.01) | |

(52) U.S. Cl.
CPC . *A61K 9/14* (2013.01); *A61K 9/145* (2013.01); *A61K 9/2054* (2013.01); *A61K 9/2077* (2013.01); *A61K 31/195* (2013.01); *A61K 31/198* (2013.01); *A61K 31/275* (2013.01); *A61K 31/277* (2013.01); *A61K 9/1635* (2013.01); *A61K 9/1652* (2013.01)

(58) Field of Classification Search
None
See application file for complete search history.

(56) References Cited

FOREIGN PATENT DOCUMENTS

| WO | WO 01/01984 | * | 1/2001 |
|---|---|---|---|
| WO | WO0101984 A1 | | 1/2001 |
| WO | WO2006131591 A2 | | 12/2006 |
| WO | WO2007138086 A1 | | 12/2007 |

* cited by examiner

*Primary Examiner* — Robert A Wax
*Assistant Examiner* — Danah Al-Awadi
(74) *Attorney, Agent, or Firm* — Bio Intellectual Property Services LLC (Bio IPS); O. (Sam) Zaghmout

(57) ABSTRACT

The present invention relates to single oral dose pharmaceutical compositions comprising a combination of entacapone, levodopa and carbidopa, or salts thereof along with one or more sugar alcohols, wherein the entacapone is co-micronized with one or more sugar alcohols. The composition of the invention exhibits bioequivalence to commercially available entacapone, levodopa and carbidopa combination formulation marketed under the trade name Stalevo200®. The invention also relates to processes for making such compositions.

11 Claims, No Drawings

PHARMACEUTICAL COMPOSITIONS OF ENTACAPONE, LEVODOPA AND CARBIDOPA WITH IMPROVED BIOAVAILABILITY

CROSS-REFERENCE TO RELATED APPLICATIONS

This application is a Continuation of U.S. application Ser. No. 12/865,745, filed Nov. 29, 2010, now pending, which is a national stage patent application of International Application No. PCT/IB09/50486, filed Feb. 6, 2009, now abandoned, which claims a priority to an Indian patent application IN2008MU263A, filed Feb. 6, 2008, which claims a priority to an Indian patent application IN2008MU262A, filed Feb. 6, 2008. The entire disclosure of these prior applications are hereby incorporated by reference.

FIELD OF THE INVENTION

The present invention relates to single oral dose pharmaceutical compositions comprising a combination of entacapone, levodopa and carbidopa, or salts thereof along with one or more sugar alcohols, wherein the entacapone is co-micronized with one or more sugar alcohols. The composition of the invention exhibits bioequivalence to commercially available entacapone, levodopa and carbidopa combination formulation marketed under the trade name Stalevo200®. The invention also relates to processes for making such compositions.

BACKGROUND OF THE INVENTION

Entacapone, an inhibitor of catechol-O-methyltransferase (COMT), is a nitro-catechol-structured compound used in the treatment of Parkinson's disease as an adjunct to levodopa/carbidopa therapy. Chemically, entacapone is (E)-2-cyano-3-(3,4-dihydroxy-5-nitrophenyl)-N,N-diethyl-2-propenamide having the following structural formula:

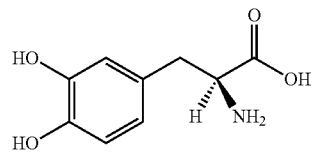

Carbidopa, an inhibitor of aromatic amino acid decarboxylation, is a white, crystalline compound which is slightly soluble in water. Chemically, it is (−)-L-(α-hydrazino-(α-methyl-β-(3,4-dihydroxybenzene) propanoic acid monohydrate having structural formula the following structural formula:

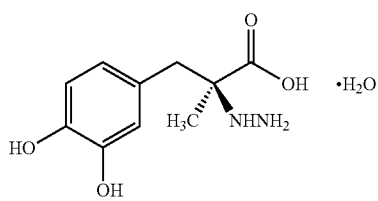

Levodopa, an aromatic amino acid, is a white, crystalline compound which is slightly soluble in water. Chemically, it is (−)-L-α-amino-β-(3,4-dihydroxybenzene) propanoic acid having the following structural formula:

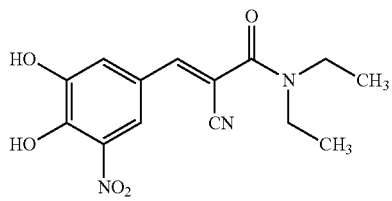 [SMILES: CCN(CC)C(=O)/C(C#N)=C/c1cc(O)c(O)c([N+](=O)[O-])c1]

Entacapone is a class IV drug under the Biopharmaceutics Classification system and poses problems of low solubility, low dissolution rate and hence low bioavailability.

U.S. Pat. No. 4,963,590 provides a pharmaceutical composition comprising entacapone and pharmaceutically acceptable carrier.

U.S. Pat. Nos. 6,500,867 and 6,797,732 disclose oral solid tablet compositions comprising entacapone, levodopa and carbidopa, or pharmaceutically acceptable salts or hydrates thereof, and a pharmaceutically acceptable excipient. Both these patents disclose that when carbidopa, levodopa and entacapone are mixed together, it results in stability problems and desired therapeutic effect is not achieved. On the other hand, when a substantial portion of carbidopa is separated from levodopa and entacapone, the formulation exhibits better stability and desired therapeutic effect is also achieved.

U.S. Pat. No. 6,599,530 provides an oral compacted composition in the form of a tablet which includes entacapone, nitecapone, or pharmaceutically acceptable salt of entacapone or nitecapone, and croscarmellose sodium in an amount of at least 6% by weight of the composition.

U.S. Application No. 20060222703 describes oral pharmaceutical compositions of entacapone, carbidopa and levodopa with microcrystalline cellulose and starch by simultaneous mixing of all the three actives. The composition is prepared by compaction granulation. The application describes the disadvantages associated with wet granulation technique which includes destabilization of composition and decreased dissolution of levodopa, carbidopa and entacapone due to use of water in the wet granulation method.

Although it is known that micronization or grinding of a substance in the presence of a surfactant or sugar can increase its solubility, these parameters are not always adequate. For example, the bioavailability of micronized progesterone is not adequate and should be improved, for example by dispersion in carnauba wax. Such a technique is described in International Publication No. (PCT) WO 8902742. Thus, it appears that the properties of a substance treated by micronization or grinding, in particular its solubility and its bioavailability, are not predictable and contradictory results may be obtained.

There are numerous prior art references which disclose the use of sugar alcohols like mannitol, sorbitol etc. as fillers in the formulation or as sensory cue agents, i.e. the agents which impart feeling of cooling in mouth in case of orally disintegrating tablets. For example, International Publication Nos. (PCT) WO 2007080601, 2007001086, 2006057912; European Patent Nos. 589981B1, 906089B1, 1109534B1; U.S. Pat. No. 6,328,994, and US Application Nos. 20070196494, 20060240101, and 20060057199. Sugar alcohols like mannitol are employed in the most orally disintegrating formulations and not in the conventional immediate release formulations as sensory cue agents because the orally disintegrating tablets disintegrate in mouth instead of disintegrating in the gastrointestinal tract as in the case of conventional immediate release tablets.

SUMMARY OF THE INVENTION

In one general aspect there is provided a single oral dose pharmaceutical composition which includes a combination of entacapone, levodopa and carbidopa, or salts thereof along with one or more sugar alcohols, wherein the entacapone is co-micronized with one or more sugar alcohols.

Embodiments of the pharmaceutical composition may include one or more of the following features. For example, the pharmaceutical composition may further include one or more pharmaceutically acceptable excipients. The pharmaceutically acceptable excipients may include one or more binders, fillers, lubricants, disintegrants, glidants, and the like.

In another general aspect there is provided a single oral dose pharmaceutical composition which includes a combination of entacapone, levodopa and carbidopa, or salts thereof along with one or more sugar alcohols; wherein the entacapone is co-micronized with one or more sugar alcohols; wherein the composition exhibits a dissolution profile such that at least 80% of the entacapone is released within 30 minutes; and wherein the release rate is measured in Apparatus 2 (USP, Dissolution, paddle, 50 rpm) using 900 ml of pH 5.5 phosphate buffer at 37° C.±0.5° C.

In another general aspect there is provided a process for preparing a pharmaceutical composition, the process comprising: a) co-micronizing entacapone or salts thereof with one or more sugar alcohols, mixing and granulating with one or more pharmaceutically acceptable excipients; b) mixing and granulating carbidopa and levodopa with one or more pharmaceutically acceptable excipients; c) mixing the mixture of step (a) and step (b); and d) forming the mixture of step (c) into a pharmaceutical dosage form.

Embodiments of the pharmaceutical composition may include one or more of the following features. For example, the pharmaceutically acceptable excipients may include one or more binders, fillers, lubricants, disintegrants, glidants, and the like.

In another general aspect there is provided a single oral dose pharmaceutical composition which includes a combination of entacapone, levodopa and carbidopa, or salts thereof along with one or more sugar alcohols; wherein the entacapone is co-micronized with one or more sugar alcohols; and wherein the composition exhibits no significant difference in one or both of the rate and the extent of absorption of entacapone than that obtained by conventional entacapone, levodopa and carbidopa formulation marketed under the trade name Stalevo200®.

Embodiments of the pharmaceutical composition may include one or more of the following features. For example, the pharmaceutical composition may further include one or more pharmaceutically acceptable excipients. The pharmaceutically acceptable excipients may include one or more binders, fillers, lubricants, disintegrants, glidants, and the like.

The details of one or more embodiments of the inventions are set forth in the description below. Other features, objects and advantages of the inventions will be apparent from the description and claims.

DETAILED DESCRIPTION OF THE INVENTION

The present inventors have noticed that sugar alcohols like mannitol or sorbitol when used along with other known water insoluble drugs like fenofibrate, irbesartan, aripiprazole, either as a physical mixture or in the form of a complex, does not result in any significant increase in solubility of the above mentioned poorly soluble drugs. It was also observed that it does not make any significant difference either in solubility or percent release of these poorly soluble drugs, whether these drugs are present alone in a formulation or along with sugar alcohols.

The present inventors while working on the combination formulation of entacapone, levodopa, carbidopa have surprisingly found that when entacapone is co-micronized with one or more sugar alcohols, it results in a significant increase in the solubility of entacapone and percent drug release of entacapone from the combination of entacapone, levodopa, and carbidopa formulation vis-à-vis the formulation wherein the entacapone is not co-micronized with a sugar alcohol.

Stalevo 200® releases about 70% of entacapone in 30 minutes, whereas the pharmaceutical composition of the present invention releases about 85% of the entacapone in 30 minutes. This significant increase in percent release of entacapone leads to improved wettability, solubility, and hence increased percent release.

The inventors have further noticed that the pharmaceutical composition of the invention is bioequivalent to commercially available combination of entacapone, carbidopa, and levodopa (Stalevo 200®).

'Bioequivalency' is established by a 90% Confidence Interval (CI) of between 0.80 and 1.25 for both maximum plasma concentration ($C_{max}$) and area under the curve (AUC) under USFDA regulatory guidelines, or a 90% CI for AUC of between 0.80 to 1.25 and a 90% CI for $C_{max}$ of between 0.70 to 1.43 under the European EMEA regulatory guidelines.

Bioequivalence studies were carried out between Stalevo 200® and the composition of the present invention. The study was monitored in terms of $C_{max}$, AUC, and time to reach maximum plasma concentration ($T_{max}$) achieved with the test product (composition of the present invention) and the reference product (Stalevo 200®). Table 3 gives the bioequivalence data of composition of the present invention and Stalevo 200®. Table 4 provides the bioequivalence data with respect to Test to reference Ratios (T/R ratios) at 90% Confidence Interval.

In the single oral dose pharmaceutical composition of the invention, a substantial portion of entacapone or a salt thereof may be separated from a mixture of levodopa and carbidopa or salts thereof; or a substantial portion of carbidopa or a salt thereof may be separated from a mixture of levodopa and entacapone or salts thereof; or the carbidopa, entacapone or levodopa may be present simultaneously in a mixture.

The term 'substantial portion' of entacapone/carbidopa/levodopa or a salt thereof herein refers to the amount of entacapone/carbidopa/levodopa or salts thereof that do not interfere with stability and or dissolution and therapeutic effect or bioavailability thereof of any of entacapone/carbidopa/levodopa in a single oral dose combination of entacapone, levodopa and carbidopa.

The composition of the invention may exhibit pharmacokinetic profile characterized by maximum plasma concentration ($C_{max}$) from about 1.1 to about 2.0 µg/ml; time to reach maximum plasma concentration ($T_{max}$) from about 1.6 to about 3.5 h; area under the concentration time curve ($AUC_{0-t}$) and ($AUC_{101}$) from about 1.80 to about 3.50 µg.h/ml.

At 90% confidence interval; area under the concentration time curve ($AUC_{0-t}$ and/or $AUC_{101}$) values of composition of the invention may be between 0.70 and 1.30 and maximum plasma concentration ($C_{max}$) values of composition of the invention may be between 0.60 and 1.40 as compared to that obtained by a Stalevo 200®.

Suitable sugar alcohols may include one or more of mannitol, maltitol, maltol, sorbitol, lactitol, xylitol, and the like.

In the pharmaceutical composition of the invention, the entacapone can be present in an amount relative to the sugar alcohol, such that a molar ratio between the entacapone and the sugar alcohol is from about 1:1 to 10:1.

The co-micronization can be carried out by suitable means known in the art, which include but not limited to one or more of nano mill, ball mill, attritor mill, vibratory mill, sand mill, bead mill, jet mill, ultrasonication, and the like.

The mean particle size of entacapone and sugar alcohol obtained after co-micronization may be less than 30 μ.

The pharmaceutical composition can be prepared in two parts. The first part may include co-micronizing entacapone with one or more suitable sugar alcohols, granulating with a binder solution and drying the granules. The dried granules can be milled and mixed with other suitable pharmaceutically acceptable excipients.

The second part may include mixing levodopa and carbidopa with one or more suitable pharmaceutically acceptable excipients and granulating with a binder solution. The granules can be dried. The dried granules can be milled and mixed with one or more suitable pharmaceutically acceptable excipients.

The granules of entacapone and the granules of levodopa and carbidopa can be formulated into a suitable dosage form such as monolayered tablets, bilayered tablets, tablet in a tablet, a caplet, minitablets, capsules, tablet in a capsule, granules in a capsule, pellets, pellets in capsules, powder. Further, the powder or granules can be suspended to give a pharmaceutically acceptable oral suspension.

The pharmaceutical composition may include one or more pharmaceutically acceptable excipients. The pharmaceutically acceptable excipients may include binders, fillers, lubricants, disintegrants, and glidants.

Suitable binders may include one or more of povidone, starch, stearic acid, gums, hydroxypropylmethylcellulose, and the like.

Suitable fillers may include one or more of microcrystalline cellulose, lactose, mannitol, calcium phosphate, calcium sulfate, kaolin, dry starch, powdered sugar, and the like.

Suitable lubricants may include one or more of magnesium stearate, zinc stearate, calcium stearate, stearic acid, sodium stearyl fumarate, hydrogenated vegetable oil, and the like.

Suitable glidants may be one or more of colloidal silicon dioxide, talc or cornstarch, and the like.

Suitable disintegrants may be one or more of starch, croscarmellose sodium, crosspovidone, sodium starch glycolate, and the like.

Example 1

The composition of the batches is provided in table 1. The following formulations are representatives of the preferred compositions of the present invention.

The preparation of example 1 is detailed below.

TABLE 1

Composition of Levodopa, carbidopa and entacapone

| No | Ingredients | % Composition |
|---|---|---|
| | Entacapone Granules | |
| 1 | Entacapone | 20-45 |
| 2 | Starch | 2-15 |
| 3 | Mannitol | 2-25 |
| 4 | Polyvinyl pyrrolidone | 0.3-5 |
| 5 | Purified Water | q.s. |

TABLE 1-continued

Composition of Levodopa, carbidopa and entacapone

| No | Ingredients | % Composition |
|---|---|---|
| 6 | Croscarmellose sodium | 1-6 |
| 7 | Sodium starch glycollate | 1-8 |
| | Levodopa, carbidopa Granules | |
| 8 | Levodopa | 5-40 |
| 9 | Carbidopa | 1-10.0 |
| 10 | Starch | 2-15 |
| 11 | Croscarmellose sodium | 2-5 |
| 12 | Povidone | 0.5-5 |
| 13 | Purified Water | q.s. |
| | Extragranular portion | |
| 14 | Mannitol | 3-25 |
| 15 | Sodium starch glycollate | 1-8 |
| 16 | Microcrystalline cellulose + Sodium carboxymethyl cellulose | 4-20 |
| 17 | Talc | 0.1-2 |
| 18 | Magnesium stearate | 0.1-2 |
| | Film coating using Opadry | 1-5% |

Procedure: The pharmaceutical composition was prepared in two parts. The first part included mixing entacapone with mannitol and co-micronizing the pre-mix through one or more cycles. Starch, croscarmellose sodium, sodium starch glycollate were mixed in a rapid mix granulator, granulated with aqueous povidone solution and the granules were dried in a fluidized bed dryer.

The second part included mixing levodopa, carbidopa with starch, granulating with aqueous povidone solution and drying the granules in a fluidized bed dryer. The dried granules of entacapone and levodopa, carbidopa were combined and mixed with sodium starch glycollate, mannitol, microcrystalline cellulose, and talc in a double cone blender and lubricated with magnesium stearate. The lubricated granules were compressed into tablets using suitable tooling and coated with aqueous dispersion of opadry.

TABLE 2

Comparative dissolution data of Stalevo 200 ® vs composition of the present invention prepared as per example 1. For determination of drug release rate, USP Type 2 Apparatus (rpm 50) was used wherein 1000 ml of pH 5.5 phosphate buffer at 37° C. ± 0.5° C. was used as a medium.

| Time (min) | % drug (entacapone) released (Stalevo 200) ® | % drug (entacapone) released (Example-1) |
|---|---|---|
| 5 | 1 | 6 |
| 10 | 11 | 13 |
| 20 | 44 | 51 |
| 30 | 70 | 85 |
| 45 | 90 | 96 |
| 60 | 96 | 100 |

TABLE 3

Bioequivalence data of composition of the present invention against Stalevo 200 ® with respect to pharmacokinetic parameters.

| Sr. No | Pharmacokinetic parameters | Stalevo 200 ® (Entacapone) | Composition of the invention (Entacapone) |
|---|---|---|---|
| 1 | $C_{max}$ (μg/ml) | 1.22 | 1.35 |
| 2 | $T_{max}$ (h) | 1.70 | 1.71 |
| 3 | $AUC_{0-t}$ (μgh/ml) | 1.83 | 2.05 |
| 4 | $AUC_\infty$ (μgh/ml) | 2.01 | 2.12 |

TABLE 4

Bioequivalence data with respect to Test (composition of the present invention) to reference (Stalevo 200 ®) Ratios (T/R ratios) at 90% Confidence Interval

| Sr. No | Pharmacokinetic parameters | Ratio | 90% C.I. Lower | 90% C.I. Upper | % CV |
|---|---|---|---|---|---|
| 1 | $C_{max}$ | 103.99 | 87.59 | 123.45 | 32.95 |
| 2 | $AUC_{0-t}$ | 108.69 | 102.33 | 115.45 | 11.33 |
| 3 | $AUC_\alpha$ | 98.43 | 91.03 | 106.43 | 13.90 |

While the invention has been described in terms of its specific embodiments, certain modifications and equivalents will be apparent to those skilled in the art and are intended to be included within the scope of the invention.

The invention claimed is:

1. A pharmaceutical composition in the form of a tablet dosage form, said composition comprising 20-45% w/w of entacapone or salts thereof, 5-40% w/w of levodopa or salts thereof and 1-10% w/w of carbidopa or salts thereof; said composition obtained by:
   (a) co-micronizing entacapone or salts thereof with one or more sugar alcohols in presence of one or more pharmaceutically acceptable excipients, such that the co-micronized entacapone or salts thereof and sugar alcohol mixture has a mean particle size of less than 30μ;
   (b) mixing and granulating carbidopa or salts thereof, and levodopa or salts thereof with one or more pharmaceutically acceptable excipients;
   (c) mixing the mixture obtained in step (a) and (b); and
   (d) compressing the mixture obtained in step (c) into a tablet dosages form.

2. The pharmaceutical composition of claim 1, wherein the entacapone and sugar alcohol are present in a molar ratio from about 1:1 to 10:1.

3. The pharmaceutical composition of claim 1, wherein the sugar alcohols comprise one or more of mannitol, maltitol, maltol, sorbitol, lactitol and xylitol.

4. The pharmaceutical composition of claim 1, wherein the composition comprises one or more of a tablet, a capsule, powder, a disc, a caplet, granules, pellets, granules in a capsule, minitablets, minitablets in a capsule, pellets in a capsule and a sachet.

5. The pharmaceutical composition of claim 1 further comprises one or more pharmaceutically acceptable excipients.

6. The pharmaceutical composition of claim 1, wherein a substantial portion of entacapone or a salt thereof is separated from a mixture of levodopa and carbidopa or salts thereof.

7. The pharmaceutical composition of claim 1, wherein a substantial portion of carbidopa or a salt thereof is separated from a mixture of entacapone and levodopa or salts thereof.

8. The pharmaceutical composition of claim 1, wherein the composition exhibits a dissolution profile such that at least 80% of entacapone is released within 30 minutes; wherein the release rate is measured in Apparatus 2 (USP, Dissolution, paddle, 50 rpm) using 900 ml of pH 5.5 phosphate buffer at 37° C.±0.5° C.

9. The pharmaceutical composition of claim 1, wherein the composition exhibits a maximum plasma concentration (Cmax) from about 1.1μg/ml to about 2.0μg/ml.

10. The pharmaceutical composition of claim 1, wherein the composition exhibits a time to reach maximum plasma concentration (Tmax) from about 1.6 h to about 3.5 h.

11. The pharmaceutical composition of claim 1, wherein the composition exhibits an area under the concentration time curve ($AUC_{0-t}$) and (AUCα) from about 1.80μg/ml to about 3.50 μg. h./ml.

* * * * *